(12) United States Patent
Shank

(10) Patent No.: US 7,780,735 B2
(45) Date of Patent: Aug. 24, 2010

(54) METHOD OF PROTECTING A KNEE PROSTHESIS DURING INTRA-OPERATIVE IMPLANTATION

(76) Inventor: Cheryl A. Shank, 536 Edgeview St., Lower Burrell, PA (US) 15068

( * ) Notice: Subject to any disclaimer, the term of this patent is extended or adjusted under 35 U.S.C. 154(b) by 870 days.

(21) Appl. No.: 11/638,872

(22) Filed: Dec. 14, 2006

(65) Prior Publication Data

US 2008/0082174 A1    Apr. 3, 2008

Related U.S. Application Data

(60) Provisional application No. 60/827,670, filed on Sep. 29, 2006.

(51) Int. Cl.
*A61F 2/38* (2006.01)
(52) U.S. Cl. .................. 623/20.14; 623/908; 623/911; 606/86 R
(58) Field of Classification Search .............. 623/14.12, 623/20.14, 20.15, 20.21–20.36, 908, 911; 606/86 R, 88, 90
See application file for complete search history.

(56) References Cited

U.S. PATENT DOCUMENTS

2003/0028196 A1* 2/2003 Bonutti ................ 606/87

2005/0165492 A1* 7/2005 Fitz .................... 623/20.19

FOREIGN PATENT DOCUMENTS

SE    9804015-7    * 4/2003

OTHER PUBLICATIONS

Translation of SE9804015-7.*

* cited by examiner

*Primary Examiner*—David H Willse
*Assistant Examiner*—Megan Wolf
(74) *Attorney, Agent, or Firm*—Carothers & Carothers

(57) ABSTRACT

A total knee arthorplasty in accordance with the teachings of the present invention is accomplished by surgically removing the meniscus and adjacent joint end portions of the femur and tibia and then replacing the first one of the removed joint end portions with a first prosthetic component. Thereafter a flexible protector shim is temporally inserted between the first prosthetic component and the other of the joint end portions. Then the other of the removed joint end portions is replaced with a second prosthetic component while the protector shim is maintained in position between the prosthetic components for thereby preventing scarring, scratching and minimizing movement during the cement curing phase of the insertion process. The protector shim is thereafter removed and a prosthetic meniscus is inserted between the two prosthetic components. If retractors are utilized for inserting the prosthetic meniscus, then the protector shim is maintained in position between the components to assist in the insertion of retractors without snagging or scarring the prosthetic components. Thereafter the protector shim is removed.

2 Claims, 2 Drawing Sheets

METHOD OF PROTECTING A KNEE PROSTHESIS DURING INTRA-OPERATIVE IMPLANTATION

CROSS REFERENCE TO RELATED APPLICATION

This application is based upon U.S. Provisional Patent Application No. 60/827,670, filed 29 Sep. 2006 for Total Knee Single Use Implant Protector, the entire contents thereof being incorporated herein by reference.

BACKGROUND OF THE INVENTION

The present invention pertains to the protection of the prosthetic knee devices between the femoral condyles and the tibial plateau during surgical implantation.

Over time, and with injury or overuse, cartilage breaks down. Unfortunately, cartilage has relatively little capacity for repair. As it breaks down the body's natural healing response is activated; however, instead of healing, chronic inflammation occurs. This inflammation in turn causes pain, which is better known as arthritis. Once arthritis sets in, a person is susceptible to chronic pain. When the degeneration of the cartilage progresses beyond a tolerable level of pain the joint can be replaced with a prosthesis. A joint prosthesis replaces the degenerated bone and cartilage with artificial components, generally made of metals, ceramics, plastics and/or elastomers.

Knee prosthetic devices can be divided into several types, the most common of which is called a total knee arthorplasty. In this procedure, a portion of the femur (femoral condyles) and an adjacent portion of the tibia (the tibial plateau) are resected or removed and replaced by prosthetic components, with a polyethylene insert bearing substituted for the original meniscal cartilage.

Generally the tibial prosthetic component is first inserted and secured with an appropriate cement, adhesive and/or fastening element. Then the femoral prosthetic component is normally inserted and secured. At this stage it is necessary not to scratch, scar, otherwise damage, or move either one of the polished prosthetic components until the cement curing phase of the surgery is completed. This is normally accomplished by having the assistant apply traction between the femur and the tibia while the leg is in a 90 degree position. A common alternative method of distraction is utilizing the smallest size trial insert bearing (prosthetic meniscus) as a buffer. Even the use of the smallest bearing trial insert (prosthetic meniscus) can be too tight causing the uncured cemented prosthesis to move and malposition.

Unfortunately, even with the greatest care, scratching or marring of the polished component surfaces nevertheless can occur. Even a minor scar or scratch will eventually cause premature wear and ultimately prosthetic failure. If the scratching or marring is major, the knee prosthesis must be completely removed requiring the patient to have additional surgery and to be subjected to additional prolonged pain and stress.

In addition, when a prosthetic meniscus is inserted between the prosthetic knee components, this is generally accomplished by first inserting retractors between the prosthetic components for assisting in placement or insertion of the meniscus between the prosthetic components. When inserting the retractors, there exists once again a very great risk that the retractors will scratch, mar or malposition the uncured cemented polished components.

SUMMARY OF THE INVENTION

The present invention provides a method of surgically protecting a knee joint wherein the meniscus and adjacent joint end portions of femur and tibia are surgically removed and then one of the removed joint end portions is replaced with a first prosthetic component. At this stage, in accordance with the teachings of the present invention, a flexible protector shim is temporarily inserted between the first prosthetic component and the other joint end portion. Generally the tibial prosthetic component is installed first. However, this is not necessarily required and it is possible to install the femoral prosthetic component first and the method of the present invention is applicable to either procedural sequence.

Then, with the protector shim temporarily inserted, the other of the removed joint end portions is replaced with a second prosthetic component, thereby preventing scarring and scratching of either component. Thereafter, the protector shim may be removed and an insert bearing,(prosthetic meniscus), inserted between the prosthetic components.

If retractors are utilized to assist in replacing the meniscus, then the protector shim is maintained in position until after the retractors are inserted and placed in position to prevent snagging and scarring by the retractors on the polished prosthetic component surfaces.

BRIEF DESCRIPTION OF THE DRAWINGS

Other objects and advantages appear hereinafter in the following description and claims, the accompanying drawings show, for the purpose of exemplification, without limiting scope of the invention or the appended claims, certain practical embodiments of the present invention wherein:

DETAILED DESCRIPTION OF A PREFERRED EMBODIMENT

Figure 1:
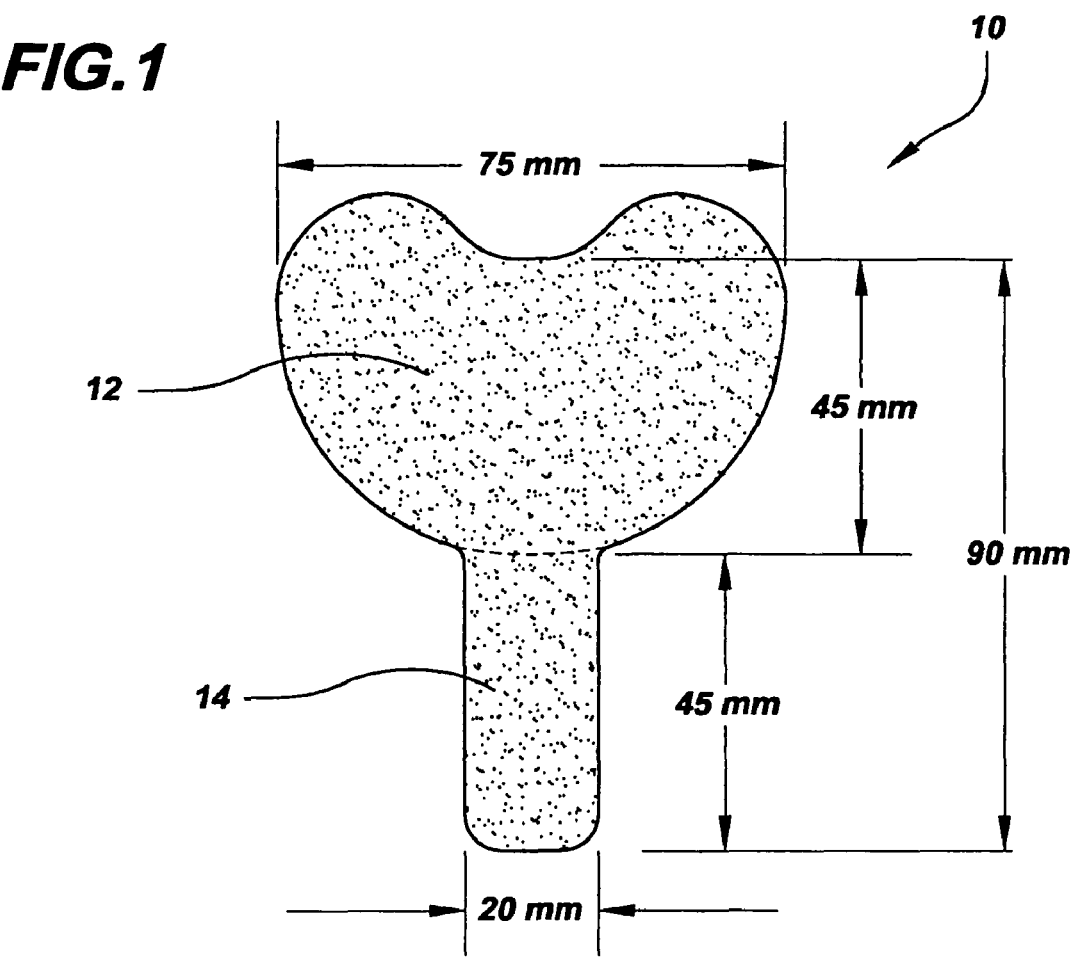
FIG. 1 is a plain view of the protector shim utilized in the method of the present invention.
Figure 2:
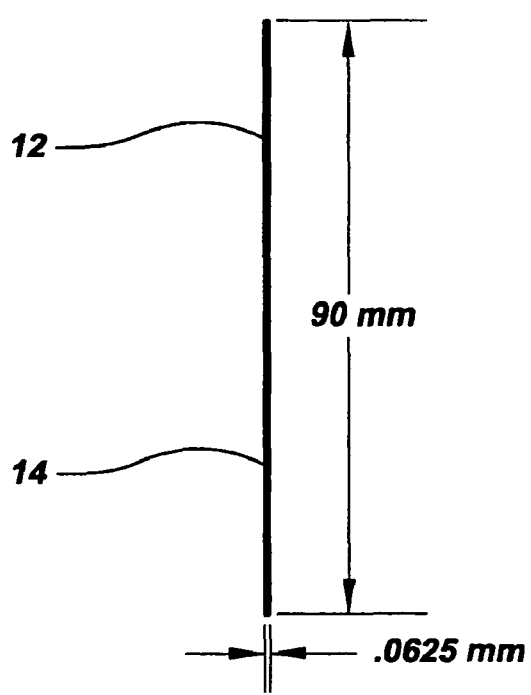
FIG. 2 is a side or edge view of the protector shim shown in FIG. 1.
Figure 3:
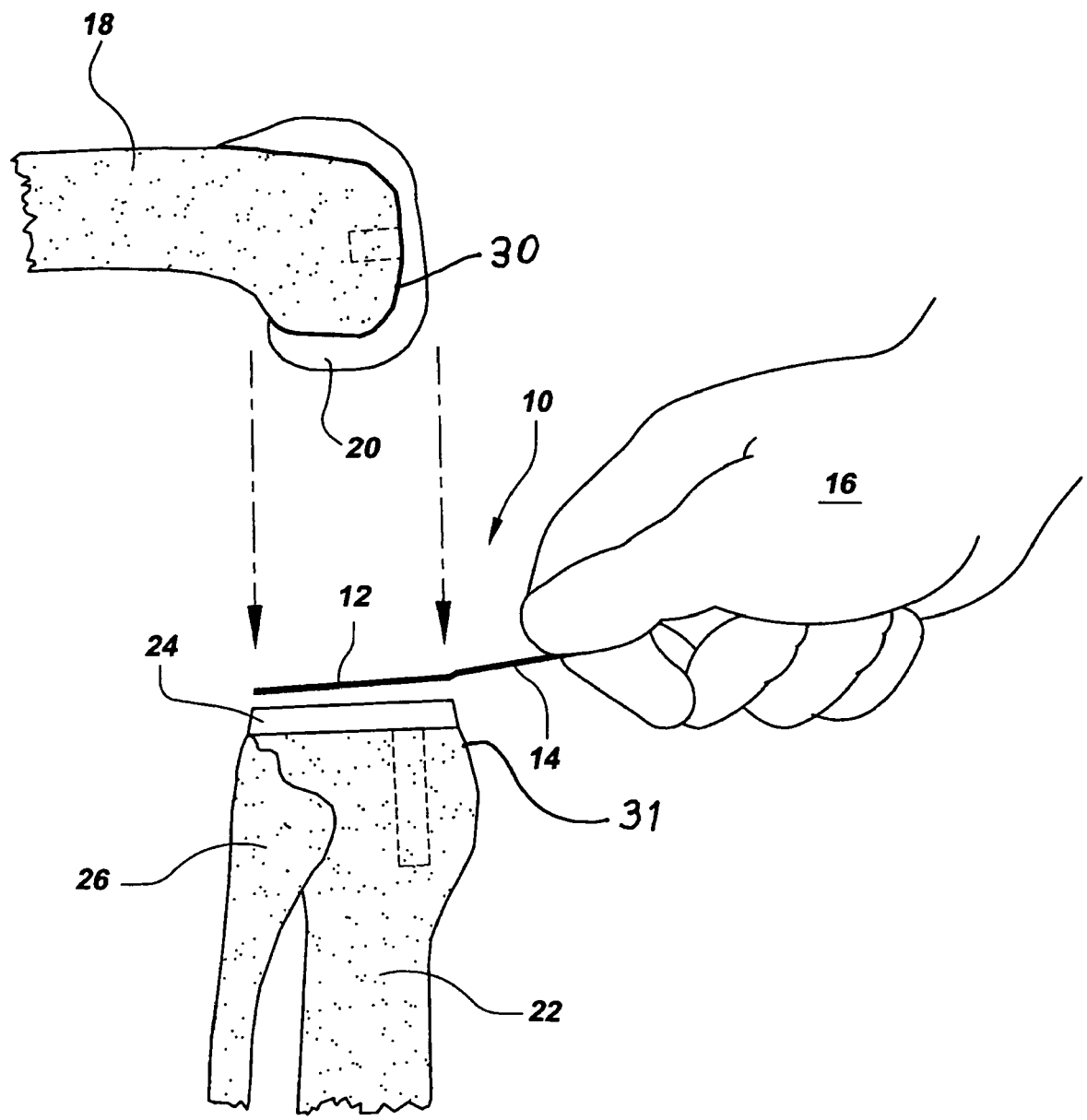
FIG. 3 is a schematic diagram illustrating the surgical protection of a knee prosthesis in accordance with the teachings of the method of the present invention.

Referring to the drawings, FIG. 3 schematically illustrates the surgical protection of knee prosthesis 10 for the knee joint illustrated having femur 18 and tibia 22 with attached fibula 26.

Total knee arthorplasty surgery is being illustrated and in the figure the meniscus (not shown) has already been removed and adjacent join end portions of the femoral condyles 30 and tibia plateau 31 have been surgically resescted. One of the removed joint end portions is then replaced with a first component. Typically the tibial prosthetic component 24 is the first, but not necessarily so, prosthetic component replaced. Thereafter the flexible protector shim 12 is temporality inserted, by the surgeon 16 by manipulation of the handle 14, between first prosthetic component 24 and the other joint end portion 30. The first prosthetic component 24 is therefore protected and the femur 18 need not be manually distracted ay the assistant and tibia prosthetic component 24 is fully protected from being scratched or marred, while the second prosthetic component 20 is inserted to replace the removed joint end portion 30 of the femur 18. Once the second component 20 has been fully cemented in place, the protector shim 12 may be thereafter removed.

However, if it is desired to use retractors (not shown) to replace the original meniscus with the prosthetic meniscus (not shown), then the protector shim may be left in position to prevent snagging or scarring of the polished surfaces of the prosthetic components 20 and 24 as the retractors are inserted. After the retractors have been inserted and are in position, then the protector shim 12 may be removed and the final meniscial prosthetic is installed.

Protector shim 12 is constructed of flexible material preferably a flexible plastic or polymer that is biologically compatible, will comply with FDA approval and is compatible with standard sterilization techniques. For example, it is anticipated that high density polyethylene may be such a suitable material.

Accordingly, the method of the present invention minimizes implant damage during the insertion stage of total knee arthroplasty surgery, facilitates retractor placement during the implant stage of surgery (thereby avoiding snagging of the retractor on the implant components), and minimizes movement of the uncured cemented prostheses. It also eliminates the requirement of an assistant to keep the leg distracted manually by applying traction between the femur and tibia during the cementing phase of the surgery.

I claim:
1. A method of surgically protecting a knee prosthesis for a knee joint having femur and tibia knee joint end portions with a meniscus disposed therebetween, the method comprising;
   surgically removing the meniscus and adjacent joint end portions of the femur and tibia;
   replacing one of the removed joint end portions with a first prosthetic component;
   temporarily inserting and holding a flexible protector shim by a handle therefor between said first prosthetic component and the other of said joint end portions;
   replacing the other of said removed joint end portions with a second prosthetic component while said protector shim is maintained in position between said prosthetic components for thereby preventing scarring or scratching of said components and also minimizing movement of said components during a curing phase of cementing the components; and
   thereafter removing said protector shim and inserting a prosthetic meniscus between said components.
2. The method of claim 1, including inserting retractors between said protector shim and one of said components prior to removing said shim for assisting thereafter in the insertion of said prosthetic meniscus.

* * * * *